United States Patent
Tang et al.

(10) Patent No.: US 11,026,642 B2
(45) Date of Patent: Jun. 8, 2021

(54) APPARATUSES AND A METHOD FOR ARTIFACT REDUCTION IN MEDICAL IMAGES USING A NEURAL NETWORK

(71) Applicant: Canon Medical Systems Corporation, Otawara (JP)

(72) Inventors: Qiulin Tang, Buffalo Grove, IL (US); Jian Zhou, Buffalo Grove, IL (US); Zhou Yu, Wilmette, IL (US)

(73) Assignee: Canon Medical Systems Corporation, Otawara (JP)

(*) Notice: Subject to any disclaimer, the term of this patent is extended or adjusted under 35 U.S.C. 154(b) by 70 days.

(21) Appl. No.: 16/370,230

(22) Filed: Mar. 29, 2019

(65) Prior Publication Data

US 2020/0305806 A1 Oct. 1, 2020

(51) Int. Cl.
*A61B 6/03* (2006.01)
*A61B 6/00* (2006.01)
(Continued)

(52) U.S. Cl.
CPC ............ *A61B 6/032* (2013.01); *A61B 6/5205* (2013.01); *G06N 3/084* (2013.01); *A61B 6/4085* (2013.01);
(Continued)

(58) Field of Classification Search
CPC ..... A61B 6/032; A61B 6/5205; A61B 6/4085; G06N 3/084; G06N 3/0472; G16H 50/50;
(Continued)

(56) References Cited

U.S. PATENT DOCUMENTS 7,751,524 B2 7/2010 Horiuchi et al.
9,805,448 B2 10/2017 Tang et al.
(Continued)

FOREIGN PATENT DOCUMENTS

WO WO 2017/223560 A1 12/2017
WO WO 2018/126396 A1 7/2018

OTHER PUBLICATIONS

Feldkamp, L.A. et al. "Practical cone-beam algorithm" Journal of the Optical Society of America, vol. 1, No. 6, 1984, pp. 612-619 and Cover Page.
(Continued)

*Primary Examiner* — Qian Yang
(74) *Attorney, Agent, or Firm* — Oblon, McClelland, Maier & Neustadt, L.L.P.

(57) ABSTRACT

A method and apparatuses are provided that use a neural network to correct artifacts in computed tomography (CT) images, especially cone-beam CT (CBCT) artifacts. The neural network is trained using a training dataset of artifact-minimized images paired with respective artifact-exhibiting images. In some embodiments, the artifact-minimized images are acquired using a small cone angle for the X-ray beam, and the artifact-exhibiting images are acquired either by forwarding projecting the artifact-minimized images using a large-cone-angle CBCT configuration or by performing a CBCT scan. In some embodiments, the network is a 2D convolutional neural network, and an artifact-exhibiting image is applied to the neural network as 2D slices taken for the coronal and/or sagittal views. Then the 2D image results from the neural network are reassembled as a 3D imaging having reduced imaging artifacts.

19 Claims, 9 Drawing Sheets

(51) Int. Cl.
*G06N 3/08* (2006.01)
*G16H 50/50* (2018.01)
*G16H 50/20* (2018.01)
*G06N 3/04* (2006.01)
*G06T 11/00* (2006.01)

(52) U.S. Cl.
CPC ....... *G06K 2209/05* (2013.01); *G06N 3/0472* (2013.01); *G06T 11/005* (2013.01); *G06T 11/006* (2013.01); *G16H 50/20* (2018.01); *G16H 50/50* (2018.01)

(58) Field of Classification Search
CPC .. G16H 50/20; G06K 2209/05; G06T 11/005; G06T 11/006; G06T 11/008
See application file for complete search history.

(56) References Cited

U.S. PATENT DOCUMENTS

| | | | |
|---|---|---|---|
| 2010/0215233 A1* | 8/2010 | Hsieh | A61B 6/032 382/131 |
| 2018/0374245 A1 | 12/2018 | Xu et al. | |
| 2019/0104940 A1* | 4/2019 | Zhou | G06T 11/008 |
| 2019/0333222 A1* | 10/2019 | Gatti | G06T 7/143 |
| 2019/0340497 A1* | 11/2019 | Baraniuk | G06N 3/0454 |

OTHER PUBLICATIONS

Zhu, L. et al. "A short-scan reconstruction for cone-beam CT using shift-invariant FBP and equal weighting" Medical Physics, vol. 34, No. 11, 2007, p. 4422-4438 and Cover Page.

Pack, J.D. et al. "Mitigating cone-beam artifacts in short-scan CT imaging for large cone-angle scans" The 12th International Meeting on Fully Three-Dimensional Image Reconstruction in Radiology and Nuclear Medicine, 2013, pp. 300-303.

Shi, D. "Successful Suppression of Cone Beam Artifacts Using Iterative Reconstruction Algorithm" IEEE MIC2014, 2 pages.

Hsieh, J. et al. "Recent Advances in CT Image Reconstruction" Current Radiology Reports, 2013, 13 pages.

Zeng, G.L. et al. "Implementation of Tuy's cone-beam inversion formula" Physics in Medicine and Biology, 1994, pp. 493-507 and Cover Page.

Yanbo Zhang, et al., "Convolutional Neural Network based Metal Artifact Reduction in X-ray Computed Tomography", IEEE, 2018, http://arxiv.org/pdf/1709.01581.pdf.

Frank Dennerlein, et al., "Constriction of cone-beam artifacts by the Z-smart reconstruction method", IEEE Nuclear Science Symposium Conference Record, pp. 4090-4096, 2007.

Johan Nuyts, et al., "Modelling the physics in the iterative reconstruction for transmission computed tomography" Phys. Med. Biol. 58, R63-R96, 2013.

Extended European Search Report dated Jun. 23, 2020 in European Patent Application No. 20163504.2, 8 pages.

Yang Lei, et al., "Image Quality Improvement in Cone-Beam CT Using Deep Learning," Proceedings of SPIE, vol. 10948, XP055701969, 2019, 7 pages.

* cited by examiner

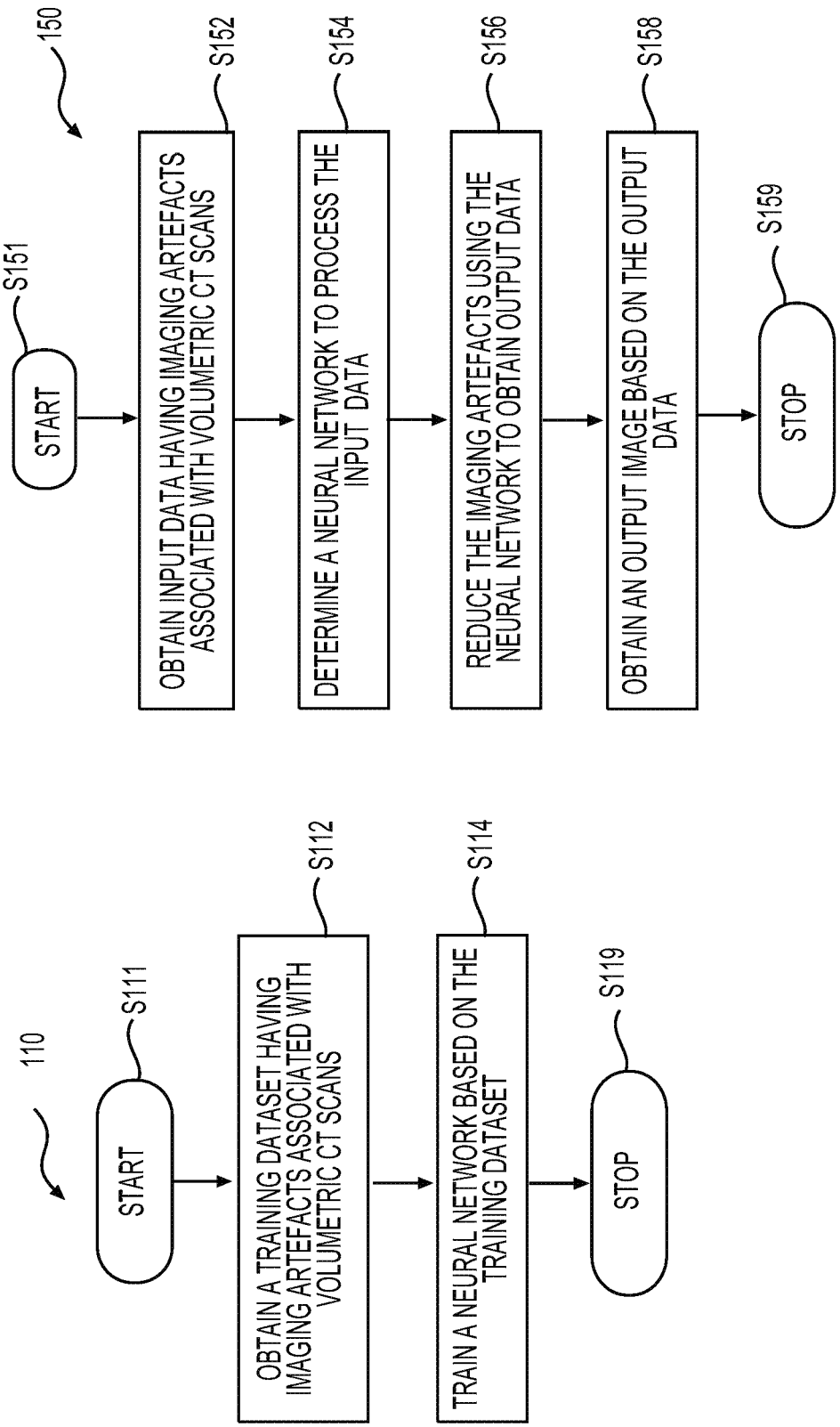

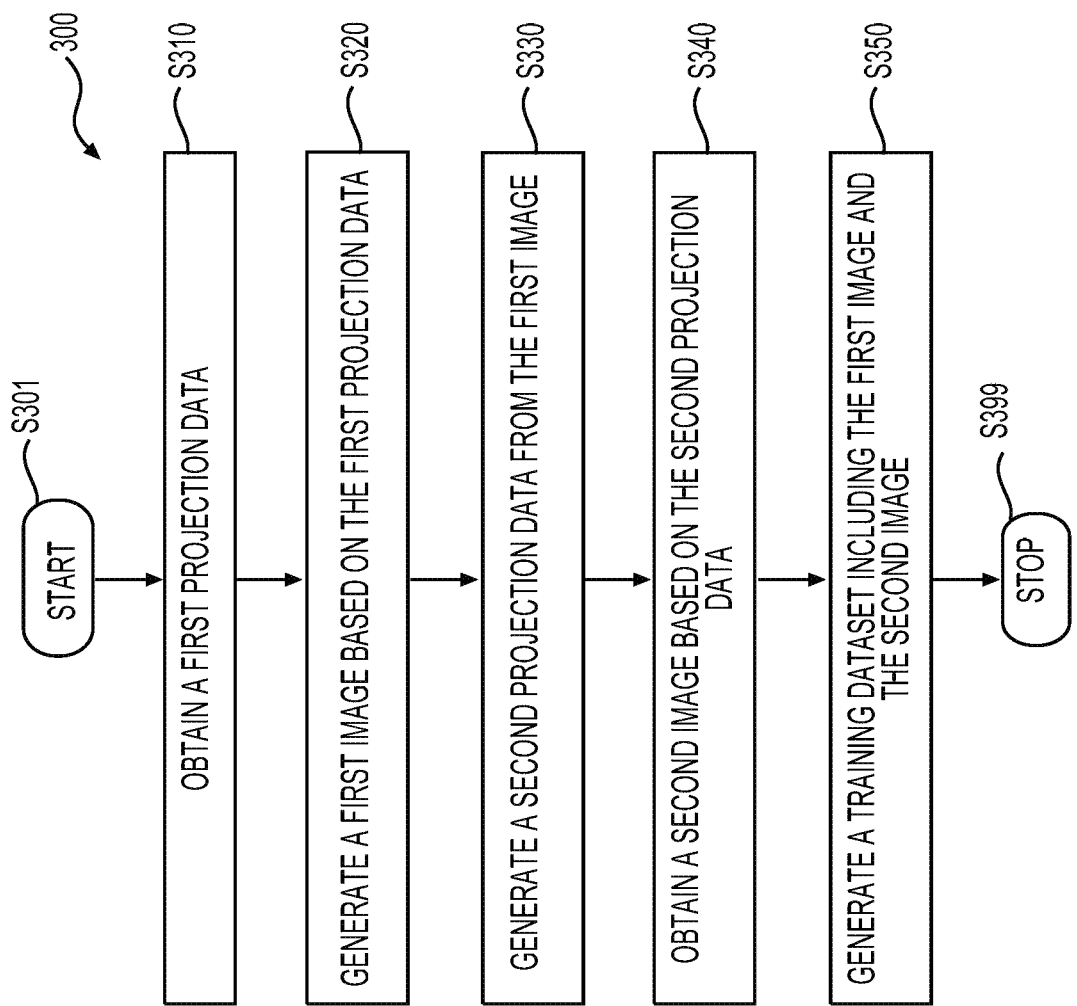

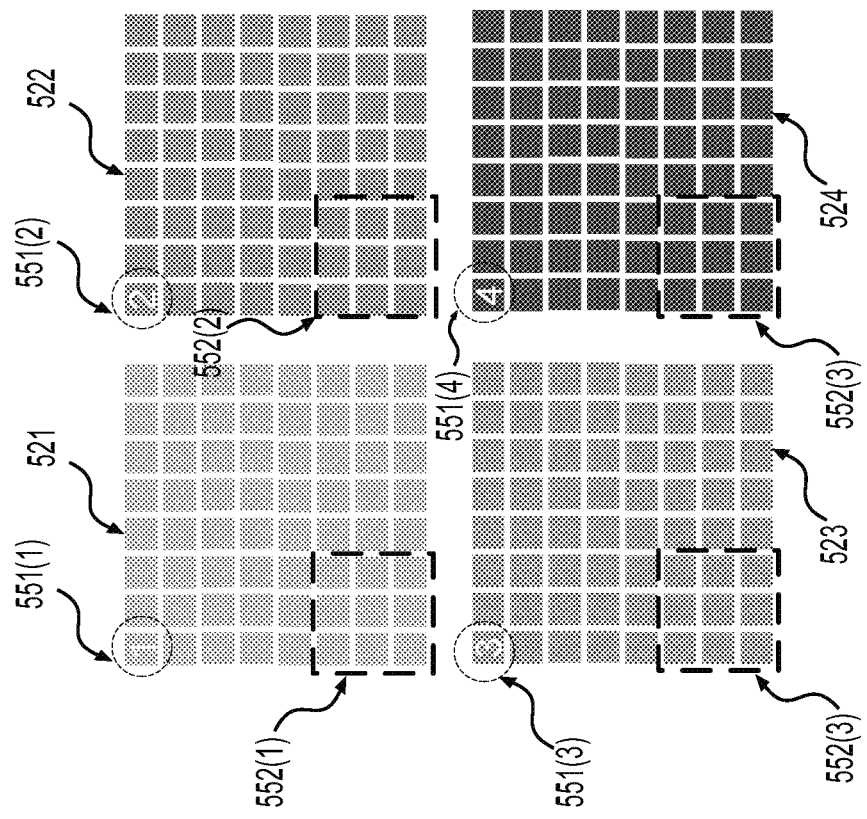
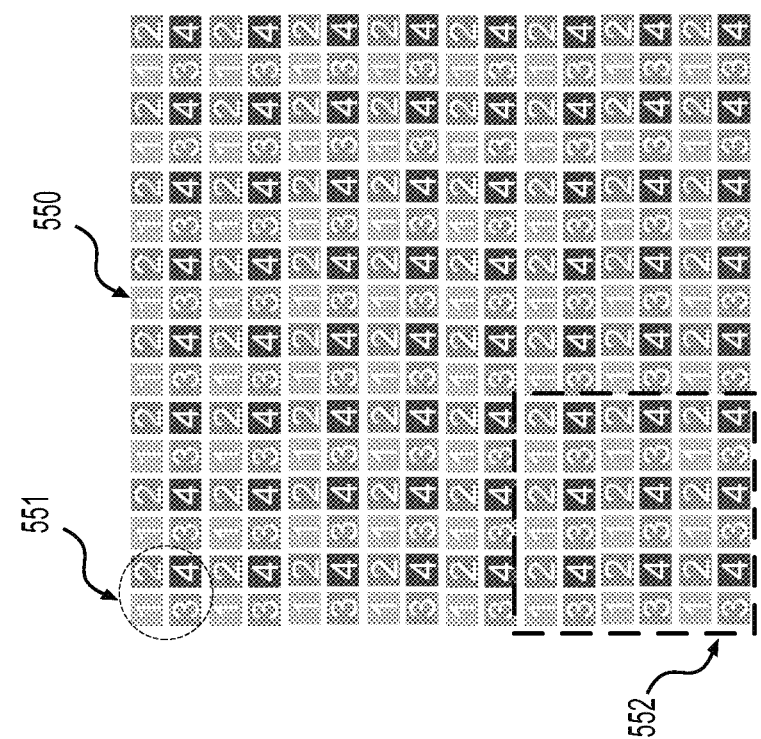
FIG. 5

APPARATUSES AND A METHOD FOR ARTIFACT REDUCTION IN MEDICAL IMAGES USING A NEURAL NETWORK

TECHNICAL FIELD

This disclosure relates to using neural networks to reduce artifacts in reconstructed medical images.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Computed tomography (CT) systems and methods are widely used, particularly for medical imaging and diagnosis. CT systems generally create images of one or more sectional slices (also referred to as sections) through a subject's body. A radiation source, such as an X-ray source, irradiates the body from one side. At least one detector on the opposite side of the body receives radiation transmitted through the body. The attenuation of the radiation that has passed through the body is measured by processing electrical signals received from the detector.

A CT sinogram indicates attenuation through the body as a function of position along a detector array and as a function of the projection angle between the X-ray source and the detector array for various projection measurements. In a sinogram, the spatial dimensions refer to the position along the array of X-ray detectors. The time/angle dimension refers to the projection angle of X-rays, which changes as a function of time during a CT scan. The attenuation resulting from a portion of the imaged object (e.g., a vertebra) will trace out a sine wave around the vertical axis. Performing an inverse Radon transform—or any other image reconstruction method—reconstructs an image from the projection data in the sinogram. X-ray CT has found extensive clinical applications in cancer, heart, and brain imaging. In some X-ray CT scans (e.g., cone-beam CT using a large cone angle), the reconstructed images have imaging artifacts. These artifacts can degrade the image quality and impede clinical applications of the reconstructed images. Accordingly, better method for reducing the imaging artifacts are desired.

BRIEF DESCRIPTION OF THE DRAWINGS

A more complete understanding of this disclosure is provided by reference to the following detailed description when considered in connection with the accompanying drawings, wherein:

FIG. 1A shows an exemplary method 110 to form a training dataset and to train a neural network, according to an embodiment of the disclosure;

FIG. 1B shows an exemplary method 150 to reduce imaging artifacts using a trained neural network, according to an embodiment of the disclosure;

FIG. 3 shows an example of a method to generate data in a training dataset, according to an embodiment of the disclosure;

FIG. 5 shows an example of pixels in a large image down-sampled into four small sub-images, according to an embodiment of the disclosure.

DETAILED DESCRIPTION

Figure 2A:
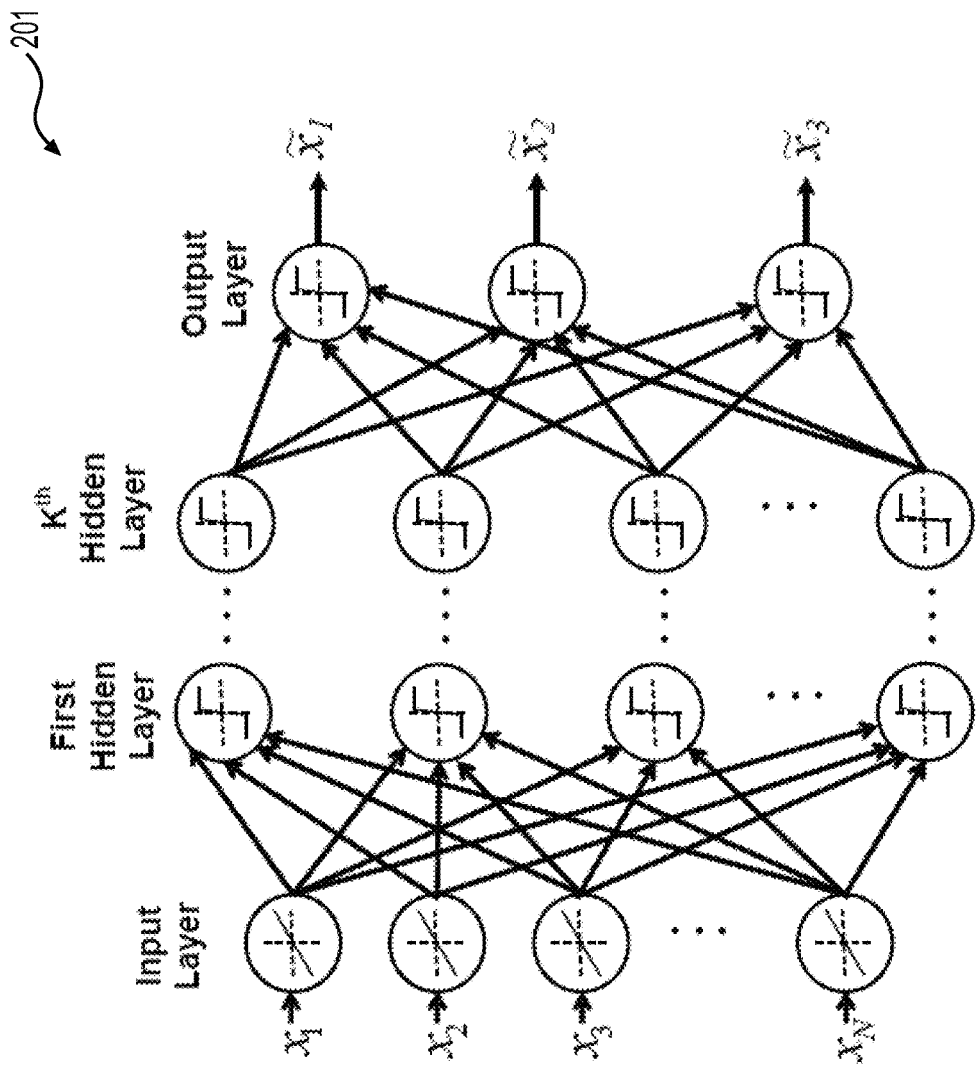
FIG. 2A shows an example of a feedforward neural network, according to an embodiment of the disclosure.

The apparatuses and methods described herein achieve several advantages over related methods. These advantages include: reducing computational time and hardware costs, and improving image quality of medical images, such as images generated by X-ray computed tomography. Further, the examples provided herein of applying these methods are non-limiting, and the methods described herein can benefit other medical imaging modalities such as single-photon emission computed tomography (SPECT), and the like, by adapting the framework proposed herein. Accordingly, the apparatuses and methods herein described herein are provided as non-limiting example implementations of the present disclosure. As will be understood by those skilled in the art, the present disclosure may be embodied in other specific forms without departing from the spirit or essential characteristics thereof. Accordingly, the detailed description is intended to be illustrative, but not limiting of the scope of the disclosure. The disclosure, including any readily discernible variants of the teachings herein, defines, in part, the scope of the foregoing claim terminology such that no inventive subject matter is dedicated to the public.

In some embodiments of CT, such as volumetric CT, to reduce imaging time and an X-ray dose, a relatively thick section (or a volume) of an object is scanned (i.e., imaged) in a single rotation of a CT source and with respect to the object OBJ being imaged. In some examples, volumetric CT, such as circular cone-beam CT (CBCT), is implemented using an X-ray beam that has a relatively larger cone angle (e.g., a cone angle that is greater than a predefined angle threshold) and scans a volume of an object in one scan. Accordingly, a three-dimensional (3D) image that shows internal features of the volume being imaged is reconstructed based on a signal from the detector. The signal corresponding to the detected radiation of the X-ray beam after having traversed the object OBJ being imaged is referred to as "projection data." The reconstructed 3D image reconstructed from a CBCT scan can be susceptible to cone-beam artifacts, i.e., undesirable characteristics that degrade image quality due to a large cone angle of the X-ray beam. The cone-beam artifacts can be mitigated using a slower scanning method such as a helical scan with a small cone angle. Other imaging artifacts besides cone-beam artifacts can also result from various aspects of the san and reconstruction processes.

To mitigate imaging artifacts, an artificial neural network (often simplified as "neural network"), such as a deep neural network, a convolutional neural network (CNN), and the like, can be trained using pairs of images including an input image that exhibits the imaging artifacts and a target image that does not exhibit the imaging artifacts. The network is trained such that applying the input image to the neural network produces a result approximately matching the target image. Then the trained neural network can be used to reduce imaging artifacts associated with volumetric CT scans, such as cone-beam artifacts.

That is, the neural network is trained using a training dataset including artifact-exhibiting data and artifact-minimized data that has less imaging artifacts than the artifact-exhibiting data. In some embodiments, artifact-exhibiting data is obtained from corresponding artifact-minimized data using simulation (e.g., forward projecting the artifact-minimized data using a large cone angle configuration to generate the artifact-exhibiting data).

Referring now to the drawings, where like reference numerals designate identical or corresponding parts throughout the several views, FIG. 1A shows a method 110 to form a training dataset and to train a neural network according to an embodiment of the disclosure. The method 110 starts at S111, and proceeds to S112.

At S112, the training dataset having imaging artifacts associated with volumetric CT scans is obtained. In general, imaging artifacts refer to undesirable characteristics that degrade image quality. Imaging artifacts can be reduced using image processing. In some embodiments, imaging artifacts, such as cone-beam artifacts, occur due to a large cone angle of an X-ray beam used in a CBCT scan. A large cone angle refers to a cone angle that is greater than a predefined angle threshold, and a small cone angle refers to a cone angle that is less than or equal to the predefined angle threshold. For example, the predefined angle threshold can be determined empirically based on observations regarding how large the cone angles can become for a particular anatomical or diagnostic application before it becomes a hindrance to clinical practice. Cone-beam artifacts often arise because for some views of the CT scan the X-ray beam does not pass through certain volume pixels (also referred to as voxels) in the reconstructed image, resulting in insufficient data/sampling for these volume pixels to be properly reconstructed. Consequently, cone-beam artifacts, such as low-frequency shading artifacts, streaking cone-beam artifacts, and the like, can be observed in these under-sampled regions.

Often a 3D reconstructed image is viewed using two-dimensional slices in one of the axial, sagittal, or coronal planes. That is, 2D images can be used to illustrate different cross-sections (or views) of internal features of an object. For example, 2D images can have coronal views, sagittal views, axial views, and the like. In some embodiments, axial views are perpendicular to the axis of rotation, and coronal views and sagittal views are parallel to the axis of rotation. In some examples, imaging artifacts vary with different views. For example, cone-beam artifacts can be more pronounced in certain views, such as coronal and sagittal views, than other views, such as an axial view, as shown in FIGS. 4A-4D. In some examples, a training dataset includes 2D images having coronal and sagittal views, 3D images, and the like.

In general, a training dataset includes artifact-exhibiting data and artifact-minimized data. In an example, artifact-exhibiting data have imaging artifacts above a certain threshold, and artifact-minimized data have imaging artifacts below the certain threshold. In some examples, artifact-exhibiting data is a reconstructed CT image referred to as an artifact-exhibiting image. In some examples, artifact-minimized data is a reconstructed CT image referred to as an artifact-minimized image. In some examples, artifact-exhibiting data and corresponding artifact-minimized data form a data pair, and imaging artifacts are more pronounced in the artifact-exhibiting data than in the respective artifact-minimized data.

In various embodiments, a training dataset can also be tailored to different CT scanning methods, protocols, applications, conditions, and the like, for example, to train various neural networks in reducing imaging artifacts associated with respective CT scanning methods, protocols, applications, conditions, and the like. As a result, the trained neural networks can be customized and tailored to certain CT scanning methods, protocols, applications, conditions, and the like. For example, a trained neural network can be tailored to reduce imaging artifacts associated with certain anatomical structures or region of a body being imaged. Further, a trained neural network is tailored to reduce cone-beam artifacts associated with circular CBCT scans that use an X-ray beam having the large cone angle.

Artifacts-exhibiting data and artifact-minimized data can be generated using any suitable methods. In some embodiments, artifact-exhibiting data and artifact-minimized data are obtained by scanning objects under different scanning conditions, protocols, and the like. In some embodiments, artifact-minimized data can be generated using a process, such as a scanning method, a protocol, and a suitable condition, that maintains imaging artifacts below a certain threshold, for example, using optimized scanning conditions, having a high X-ray dose, a small cone angle X-ray beam, and the like. On the other hand, artifact-exhibiting data can be obtained using scanning conditions exhibiting relatively large artifacts, such as an X-ray beam having a large cone angle, and the like.

In certain implementations, the artifact-exhibiting data is obtained by scanning an object using a circular CBCT scan with an X-ray beam having the large cone angle, and the corresponding artifact-minimized data are obtained by scanning the same object using a helical CT scan with an X-ray beam having the small cone angle. Accordingly, the images obtained using helical CT scans can have image artifacts below a certain threshold, making them effective as artifact-minimized data.

Additional image processing methods can be included in S112 to reduce a training time in S114. For examples, certain imaging artifacts, such as cone-beam artifacts, have low-frequency components. According to aspects of the disclosure, an image where imaging artifacts vary slowly with respect to space can be down-sampled to obtain multiple sub-images, as described in FIG. 5. The sub-images can be used to form respective data pairs.

In some embodiments, artifact-exhibiting data, such as a 3D image having cone-beam artifacts, is obtained from corresponding artifact-minimized data using simulation, image processing, and the like. Alternatively, artifact-minimized data can also be obtained from corresponding artifact-exhibiting data using simulation, image processing, and the like.

In some examples, a neuronal network is trained using a training dataset, validated using a validation dataset, and further tested using a test dataset. Therefore, in some embodiments, additional datasets, such as a validation dataset and a test dataset, are formed from additional artifact-exhibiting data and artifact-minimized data.

At S114, the neural network is trained based on the training dataset obtained at S112. In some embodiments, the neural network is trained offline, and then stored in memory to be used later when a new CT scan is performed and artifact reduction is desired.

In general, a neural network can learn and perform a task from examples, such as a training dataset including artifact-exhibiting data and artifact-minimized data, without task specific instructions. A neural network can be based on a computational model including nodes. The nodes, also referred to as neurons, interconnected by connections, can perform computational tasks. In an embodiment, a neural network can be characterized by a computational model and parameters. In an example, the parameters can include weights and thresholds associated with connections and nodes in the neural network.

In an embodiment, a neural network can be organized in multiple layers where different layers can perform different kinds of computations. The multiple layers can include an input layer having input nodes, an output layer having output nodes, and hidden layers between the input layer and the output layer. In an embodiment, the input layer can receive an input signal originated from outside of the neural network. In an example, the input signal is artifact-exhibiting data such as an image having cone-beam artifacts. The output layer can send a result to outside of the neural network. In an example, the result is an image having reduced cone-beam artifacts. In some embodiments, a neural network can be a deep neural network that has, for example, a relatively larger number of hidden layers than that of a shallow neural network. In an example, a neural network can be a CNN.

In various embodiments, a computational model of a neural network can be determined by search algorithms, and the like. Subsequently, the neural network can be trained using examples related to a certain task, such as reducing image artifacts. As a result, the parameters are modified repetitively when additional examples are used. In an embodiment, a large number of examples can be organized into multiple independent datasets, such as a training dataset and a validation dataset, to train and validate a neural network to obtain an optimal neural network.

In an embodiment, neural networks having various computational models can be trained using multiple training methods based on a training dataset including data pairs. A data pair includes having an input signal, such as artifact-exhibiting data, and an expected output signal, such as artifact-minimized data. An input layer of a neural network can receive the input signal, and the neural network can subsequently generate a result via the output layer. The result can be compared with the expected output signal. The parameters of the neural network are modified or optimized to minimize a difference between the result and the expected output signal.

In some embodiments, the neural network is trained using the training dataset obtained in S112 to optimize parameters of the neural network. Neural networks can be trained using respective training methods to have optimized parameters.

An optimal neural network is obtained by further applying a validation dataset on the trained neural networks, analyzing the results and the expected output signals associated with the validation dataset. The optimal neural network can then be deployed to perform a certain task. In addition, performance of the optimal neural network can be further assessed by a test dataset. In an example, the test dataset is independent from other datasets, such as the training dataset and the validation dataset.

In some embodiments, the neural network can be repetitively trained when additional artifact-exhibiting data and artifact-minimized data are available. For example, steps S112 and S114 can be implemented repetitively.

In some embodiments, the neural network is trained to reduce imaging artifacts, such as cone-beam artifacts associated with volumetric CT scans including CBCT scans, when the training dataset includes artifact-exhibiting images and artifact-minimized images. The method 110 then proceeds to S119, and terminates.

FIG. 1B shows a method 150 according to an embodiment of the disclosure. In some embodiments, the method 150 is used to reduce image artifacts, such as cone-beam artifacts, of an input image by using a suitable neural network, such as the neural network trained using the method 110. The method 150 starts at S151, and proceeds to S152.

At S152, input data to the neural network is obtained. In an embodiment, the input data is an input image, a reconstructed CT image having imaging artifacts associated with volumetric CT scans, such as cone-beam artifacts. In some examples, the input image is a 3D image, for example, reconstructed from corresponding projection data obtained using a circular CBCT scan, a 2D image, such as a coronal view or a sagittal view of a respective 3D image having imaging artifacts, and the like.

In some embodiments, imaging artifacts of an original image have certain features. The original image can be processed based on the features to generate the input data to the neural network to make the method 150 more efficient. For example, the imaging artifacts vary slowly with respect to space, i.e., the imaging artifacts are dominated by low spatial frequency components. Therefore, the original image can be Fourier transformed into a spatial frequency domain and includes a low-frequency component and a high-frequency component. Further, the original image can be low pass filtered in the spatial frequency domain to obtain the low-frequency component. The low-frequency component is selected to be the input data to the neural network at S152. Further, the low-frequency component can be downsampled to decrease the size of the input data that is applied to the neural network at S152, improving the computational efficiency of training and then using the neural network at S152. That is, when input data is smaller (i.e., has fewer pixels), applying the input data to the neural network at S152 can be performed using fewer computations.

In certain implementations, other methods of obtaining the low-frequency component can be used without departing from the spirit of the methods described herein, as would be understood by a person of ordinary skill in the art. For example, the low-frequency component can be generated by averaging (e.g., averaging N-by-M blocks) or by downsampling by factors of N and M in respective directions of the original image. In certain implementations N and M can be equal (e.g., in FIG. 5 N=M=2). Once, the low-frequency component is generated the high-frequency component can be generated in various way, as would be understood by a person of ordinary skill in the art, including, e.g., by subtracting the low-frequency component from the original image. Thus, all of the information in the original image can be preserved in the combination of the low-frequency component together with the high-frequency component. When the artifacts are predominantly in the low-frequency component (e.g., in cone-beam artifacts), applying the low-frequency component, which is downsampled (e.g., by a factor N in a first direction and M in a second directions), to the neural network the artifact can be efficiently mitigated, and then the resolution of the original image can be restored by combining the result of the neural network 152 with the high-frequency component, which has not been applied to the neural network 152.

At S154, a suitable neural network is determined to process the input data, such as an input image. In some examples, a neural network trained to reduce imaging artifacts associated with volumetric CT scans, such as cone-beam artifacts, is selected to process the input data. In some examples, as described above, neural networks can be customized and tailored to certain CT scanning methods, protocols, applications, conditions, and the like by using respective training datasets. Therefore, in some examples, the neural network is determined based on characteristics of the input data. In an example, a neural network trained with 3D images is selected to reduce imaging artifacts of the input data, such as a 3D image. In an example, a neural network trained with images having imaging artifacts that vary slowly with respect to space is selected to reduce imaging artifacts of the input data having similar property.

At S156, the input data is processed using the determined neural network and output data having reduced artifacts is generated.

At S158, an output image is obtained based on the output data. In various embodiments, the output data, such as a 2D or 3D image, can be further processed by suitable image processing methods to generate the output image. In some examples, as described in step S152, the original image is low pass filtered in the spatial frequency domain to obtain the low-frequency component that is processed by the neural network. Accordingly, at S158, the output data is combined with the corresponding high-frequency component of the original image to form the output image.

In some examples, step S158 is omitted, and the output image is the output data. The method then proceeds to S159, and terminates.

FIG. 2A shows an exemplary feedforward neural network 201 according to an embodiment of the disclosure. For example, the neural network 201 has N inputs, K hidden layers, and three outputs. Each layer is made up of nodes, and each node performs a weighted sum of the inputs and compares a result of the weighted sum to a threshold to generate an output (also referred to as a result). Neural networks make up a class of functions for which the members of the class are obtained by varying thresholds, connection weights, or specifics of the architecture such as the number of nodes and/or their connectivity. In an example, a relatively simple neural network, such as an autoencoder, has three layers. A deep neural network generally has more than three layers of neurons, and has as many outputs neurons as input neurons, where N, for example, is a number of pixels in an reconstructed image. In some examples, the connections between neurons store values called "weights" (also interchangeably referred to as "coefficients" or "weighting coefficients") that manipulate data in the calculations. The outputs of the neural network depend on three types of parameters: (i) the interconnection pattern between the different layers of neurons, (ii) the learning process for updating the weights of the interconnections, and (iii) the activation function that converts a neuron's weighted input to the output activation.

Figure 2B:
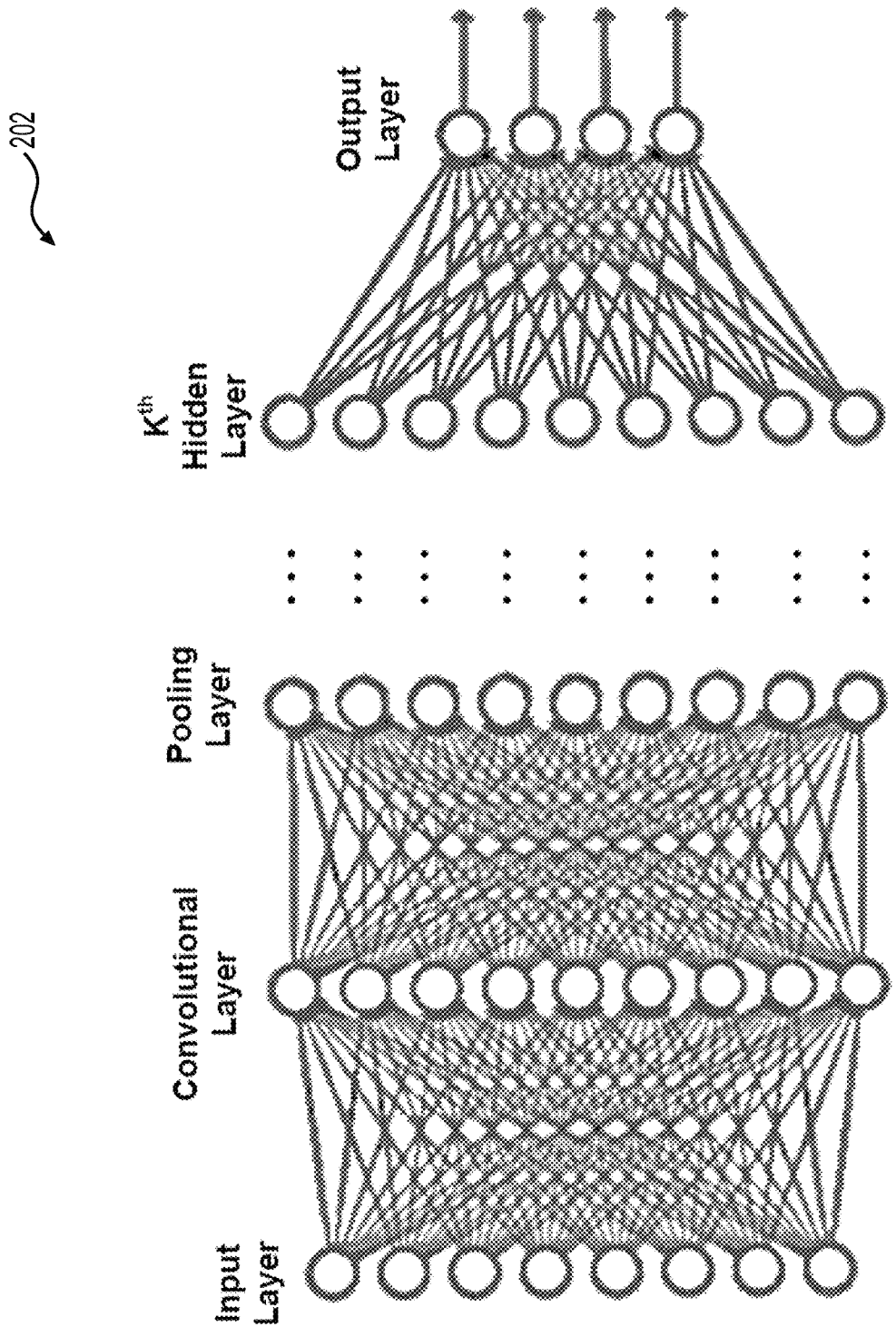
FIG. 2B shows an example of a convolution neural network (CNN), according to an embodiment of the disclosure.
Figure 2C:
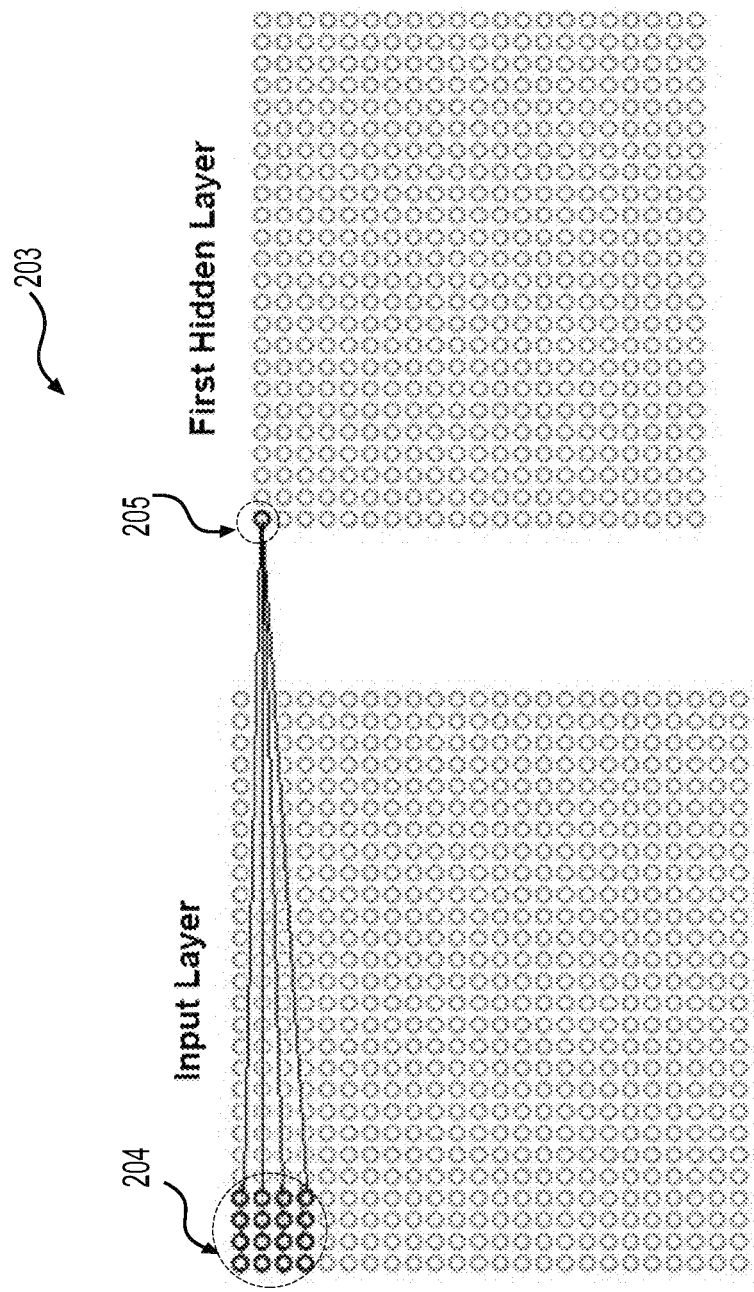
FIG. 2C shows an example of implementing a convolution layer, according to an embodiment of the disclosure.

Mathematically, a neuron's network function m(x) is defined as a composition of other functions $n_i(x)$, which can further be defined as a composition of other functions. This can be conveniently represented as a network structure, with arrows depicting the dependencies between variables, as shown in FIGS. 2A-2C. For example, the neural network can use a nonlinear weighted sum, $m(x)=K(\Sigma_i w_i n_i(x))$, where K (commonly referred to as the activation function) is certain predefined function, such as the hyperbolic tangent.

In FIG. 2A (and similarly in FIG. 2B), the neurons are depicted by circles around a threshold function or circles. For the non-limiting example shown in FIG. 2A, the inputs are depicted as circles around a linear function, and the arrows indicate directed connections between neurons. In certain implementations, the neural network trained in S114 is a feedforward network as exemplified in FIGS. 2A and 2B (e.g., it can be represented as a directed acyclic graph).

The neural network operates to achieve a specific task, such as reducing imaging artifacts, by searching within the class of functions F to learn, using a set of observations, to find $m^* \in F$ which solves the specific task in certain optimal sense (e.g., the stopping criteria used in step S260 in the method 200 described below). For example, in certain implementations, this can be achieved by defining a cost function C: $F \to \mathbb{R}$ such that, for the optimal solution $m^*$, $C(m^*) \leq C(m) \forall m \in F$ (i.e., no solution has a cost less than the cost of the optimal solution). $\mathbb{R}$ refers to the set of real numbers. The cost function C is a measure of how far away a particular solution is from an optimal solution to the problem to be solved (e.g., the error). Learning algorithms iteratively search through the solution space to find a function that has the smallest possible cost. In certain implementations, the cost is minimized over a sample of the data (i.e., the training dataset).

FIG. 2B shows an exemplary CNN 202 according to an embodiment of the disclosure. In some embodiments, CNNs have beneficial properties for image processing, thus, are relevant for applications of reducing imaging artifacts. In various embodiments, CNNs use feed-forward neural networks where the connectivity pattern between neurons can represent convolutions in image processing. For example, CNNs can be used for image processing optimization by using multiple layers of small neuron collections which process portions of an input image, called "receptive fields", also referred to as "perception fields." The outputs of these collections can then tiled so that they overlap, to obtain a better representation of the original image. This processing pattern can be repeated over multiple layers having alternating convolution and pooling layers.

FIG. 2C shows an example 203 of implementing a convolution layer according to an embodiment of the disclosure. Referring to FIG. 2C, a 4×4 kernel 204 is applied to map values from an input layer representing a 2D image to a first hidden layer, which is a convolution layer. The kernel maps respective 4×4 pixel regions 204 to corresponding neurons 205 of the first hidden layer. In the non-limiting example illustrated in FIG. 2C, for example, the receptive/perception field is 4 pixels by 4 pixels.

Following a convolutional layer, a CNN can include local and/or global pooling layers, which combine the outputs of neuron clusters in the convolution layers. Additionally, in certain implementations, the CNN can also include various combinations of convolutional and fully connected layers, with pointwise nonlinearity applied at the end of or after each layer.

CNNs have several advantages for image processing. To reduce the number of free parameters and improve generalization, a convolution operation on small regions of input is introduced. One significant advantage of certain implementations of CNNs is the use of shared weight in convolutional layers. Therefore, the same filter (weights bank) is used as the coefficients for each pixel in the layer, thus, reducing memory footprint and improving performance. Compared to other image-processing methods, CNNs advantageously use relatively little pre-processing. This means that the neural network is responsible for learning the filters that in traditional algorithms were hand-engineered. The lack of dependence on prior knowledge and human effort in designing features is a major advantage for CNNs.

In certain implementations, the neural network trained in S114 includes multiple neural networks that are suitably connected to perform a task, such as reducing imaging artifacts.

Figure 2D:
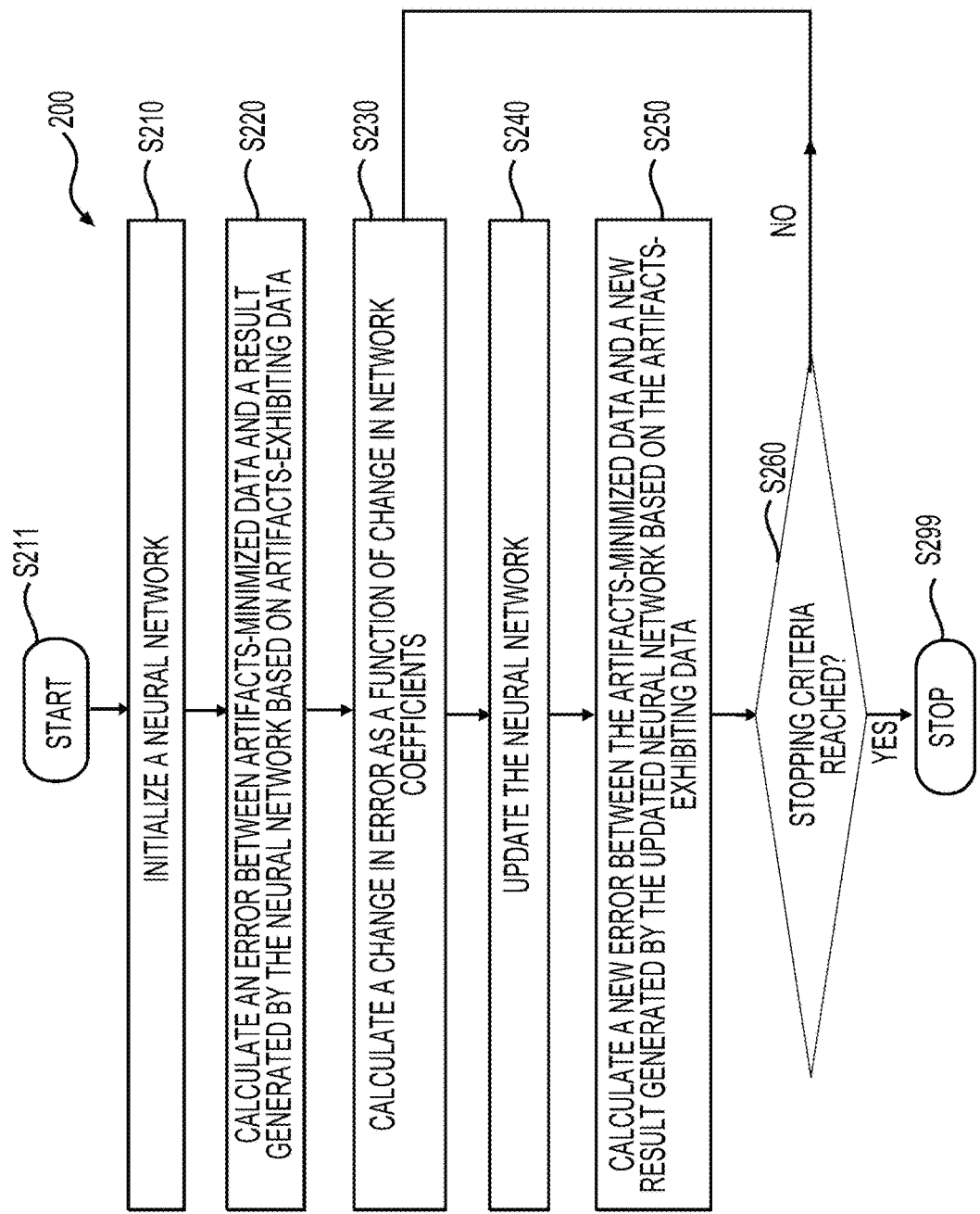
FIG. 2D shows an example of a method to train a neural network, according to an embodiment of the disclosure.

FIG. 2D shows a method 200 according to an embodiment of the disclosure. In some embodiments, the method 200 is an implementation of S114 of the method 110 for training the neural network using the training dataset obtained in S112. In an example, FIG. 2D shows one implementation of supervised learning used to train the neural network in S114 according to an embodiment of the disclosure. In supervised learning, a training dataset including artifact-exhibiting data and artifact-minimized data is obtained, and the neural network is iteratively updated to reduce the error, such that a result from the neural network based on the artifact-exhibiting data closely matches the artifact-minimized data. In other words, the neural network infers the mapping implied by the training dataset, and the cost function produces an error value related to the mismatch between the artifact-minimized data and the result produced by applying a current incarnation of the neural network to the artifact-exhibiting data. For example, in certain implementations, the cost function can use the mean-squared error to minimize the average squared error. In the case of a of multilayer perceptrons (MLP) neural network, the backpropagation algorithm can be used for training the neural network by minimizing the mean-squared-error-based cost function using a gradient descent method.

In some embodiments, training a neural network model refers to selecting one model from a set of allowed models (or, in a Bayesian framework, determining a distribution over the set of allowed models) that minimizes the cost criterion (i.e., the error value calculated using the cost function). Generally, the neural network can be trained using any of numerous algorithms for training neural network models (e.g., by applying optimization theory and statistical estimation).

For example, the optimization method used in training neural networks can use some form of gradient descent, using backpropagation to compute the actual gradients. This is done by taking the derivative of the cost function with respect to the network parameters and then changing those parameters in a gradient-related direction. The backpropagation training algorithm can be: a steepest descent method (e.g., with variable learning rate, with variable learning rate and momentum, and resilient backpropagation), a quasi-Newton method (e.g., Broyden-Fletcher-Goldfarb-Shannon, one step secant, and Levenberg-Marquardt), or a conjugate gradient method (e.g., Fletcher-Reeves update, Polak-Ribiére update, Powell-Beale restart, and scaled conjugate gradient). Additionally, evolutionary methods, such as gene expression programming, simulated annealing, expectation-maximization, non-parametric methods and particle swarm optimization, can also be used for training the neural networks.

Referring to FIG. 2D, the method 200 starts at S211, and proceeds to S210. The training dataset can include an image exhibiting imaging artifacts. For example, an imaging artifact can arise from a certain method of reconstruction, or arise from a method used for acquiring projection data (e.g., a large-angle cone-beam scan), and the like. In some embodiments, the training dataset includes artifact-exhibiting data and artifact-minimized data.

At S210, a neural network being trained is initialized. In some examples, an initial guess is generated for coefficients of the neural network. For example, the initial guess can be based on a priori knowledge of an object being imaged. Additionally, the initial guess can be based on a neural network trained on a training dataset related to a different CT scan method.

At S220, an error (e.g., a cost function) is calculated between the artifact-minimized data and a result generated from the neural network based on the artifact-exhibiting data. The error can be calculated using any known cost function or distance measure between image (or projection data), including the cost functions described above.

At S230, a change in the error as a function of the change in the neural network can be calculated (e.g., an error gradient), and the change in the error can be used to select a direction and step size for a subsequent change to the weights/coefficients of the neural network. Calculating the gradient of the error in this manner is consistent with certain implementations of a gradient descent optimization method. In certain other implementations, as would be understood by one of ordinary skill in the art, this step can be omitted and/or substituted with another step in accordance with another optimization algorithm (e.g., a non-gradient descent optimization algorithm like simulated annealing or a genetic algorithm).

At S240, a new set of coefficients are determined for the neural network. For example, the weights/coefficients can be updated using the change calculated in S230, as in a gradient descent optimization method or an over-relaxation acceleration method.

At S250, a new error value is calculated using the updated weights/coefficients of the neural network. In various embodiments, a new error value is calculated between the artifact-minimized data and a new result generated by the updated neural network based on the artifact-exhibiting data.

At S260, predefined stopping criteria are used to determine whether the training of the neural network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations is reached. When the stopping criteria is not satisfied, the method 200 will continue back to the start of the iterative loop by returning and repeating S230 using the new weights and coefficients (the iterative loop includes steps S230, S240, S250, and S260). When the stopping criteria are satisfied, the method 200 terminates at S299.

In addition to the implementation for error minimization shown in FIG. 2D, the method 200 can use one of many other known minimization methods, including, e.g., local minimization methods, convex optimization methods, and global optimization methods.

When the cost function (e.g., the error) has local minima that are different from the global minimum, a robust stochastic optimization process is beneficial to find the global minimum of the cost function. Examples of optimization method for finding a local minimum can be one of a Nelder-Mead simplex method, a gradient-descent method, a Newton's method, a conjugate gradient method, a shooting method, or other known local optimization method. There are also many known methods for finding global minima including: genetic algorithms, simulated annealing, exhaustive searches, interval methods, and other conventional deterministic, stochastic, heuristic, and metaheuristic methods. In some embodiments, the above methods can be used to optimize the weights and coefficients of the neural network. Additionally, neural networks can be optimized using a back-propagation method.

FIG. 3 shows a method 300 according to an embodiment of the disclosure. In some embodiments, the method 300 is used to implement step S112 in the method 110. For example, the method 300 generates a training dataset including a data pair having artifact-exhibiting data and artifact-minimized data. The method 300 starts at S301, and proceeds to S310.

At S310, a first projection data is obtained. The first projection data represents radiation data obtained in one or more CT scans. In some embodiments, the first projection data is measured under optimal conditions, such as using helical CT scans having the small cone angle.

At S320, a first image is generated based on the first projection data, for example, by image reconstruction. In some embodiments, the first image is artifact-minimized data that has minimal imaging artifacts, such as below the certain threshold. In some examples, the first image is a 3D reconstructed image. In some examples, the first image is a 2D reconstructed image. In some examples, the first image is a 2D coronal view or a 2D sagittal view. In some examples, an intermediate 3D image is reconstructed from the first projection data. Referring to FIGS. 4A-4D, the first image is obtained using certain view(s) that show more pronounced imaging artifacts, such as a coronal view, than other view(s), such as an axial view, of the intermediate 3D image, thus, the first image is a 2D image showing the coronal view.

The image reconstruction can be performed using a back-projection method, a filtered back-projection method, a Fourier-transform based image reconstruction method, an iterative image reconstruction method (e.g., algebraic reconstruction technique), a matrix inversion image reconstruction method, a statistical image reconstruction method, and the like.

At S330, a second projection data is generated from the first image. In some embodiments, the second projection data is generated using a forward projection method. In various examples, the second projection data is obtained using simulation under a simulation condition that can produce relatively large imaging artifacts, such as a circular CBCT scan configuration that uses an X-ray beam having the large cone angle.

In some examples, multiple second projection data are simulated from the same first image under different simulation conditions that can produce relatively large imaging artifacts. For example, the multiple second projection data can be simulated to represent various values of one or more scanning parameters. These scanning parameters can include, e.g., a scanning protocol, and a diagnostic application. In some cases, the different scanning parameters can correspond to different first images, such as when the scanning parameters are anatomic structure to be imaged or a diagnostic application. In certain implementations, the multiple second projection data are obtained using different cone angles that are greater than the angle threshold. Further, different neural networks can be optimized for specific values of the one or more scanning parameters. For example, a given neural network can be trained to be used for a first cone angle and a first anatomical structure to be imaged (e.g., a head). Another neural network can be trained to be used for the first cone angle and a second anatomical structure to be imaged (e.g., a torso). A third neural network can be trained to be used for a second cone angle and the first anatomical structure to be imaged, and so forth. For each neural network, the choice of the scanning parameters for the first images and the scanning parameters for the simulation of the corresponding second images will be chosen based on the designation of the neural network.

At S340, a second image is obtained based on the second projection data, for example, by image reconstruction. In some embodiments, the second image is artifact-exhibiting data that has relatively large imaging artifacts, such as above the certain threshold. In some examples, the second image has a same dimension, such as 2D, 3D, and the like, as that of the first image. In some examples, the second image has a same view, such as a coronal view, a sagittal view, and the like, as that of the first image. The image reconstruction can be similar or identical to the image reconstruction described in S320.

At S350, a training dataset is generated. In some embodiments, the training dataset includes the first image and the second image that form a data pair. In some embodiments, the training dataset includes the first image and multiple second images that correspond to the first image. For example, as discussed above, the same first image can be forward projected using different values for the scanning parameters, such as different cone angles, and each of these different values can be used to reconstruct a respective second image. In this case, each of the respective second images would be paired with the first image in a respective training dataset to train a neural network designated by the respective values of the scanning parameters. Further, steps S310, S320, S330, S340, and S350 can be repeated to generate additional data pairs, each including a first image and a second image, and the like to be included in the training dataset. In some examples, a validation dataset and a testing dataset are generated using additional first images and respective second images. The method 300 proceeds to S399, and terminates.

In some embodiments, a neural network can also be trained using 2D images, for example, because training a neural network with 2D images can be faster. As described above, imaging artifacts vary with different views. For example, cone-beam artifacts can be more pronounced in certain views, such as coronal and sagittal views as compared with an axial view, as shown below in FIGS. 4A-4D. In some examples, suitable views, such as coronal views and sagittal views that have relatively large imaging artifacts are included in the training dataset in S112.

Figure 4A:
FIG. 4A shows an example of a coronal view of a reconstructed image from a cone-beam CT (CBCT) scan that exhibits a cone-beam artifact, according to an embodiment of the disclosure.
Figure 4C:
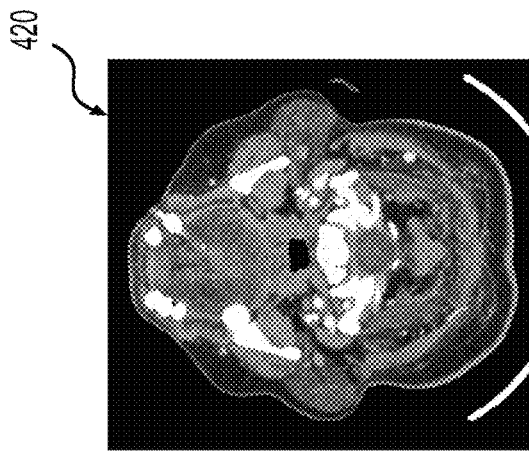
FIG. 4C shows an example of a coronal view of a reconstructed image from a helical CT scan that does not exhibit the cone-beam artifact, according to an embodiment of the disclosure.
Figure 4B:
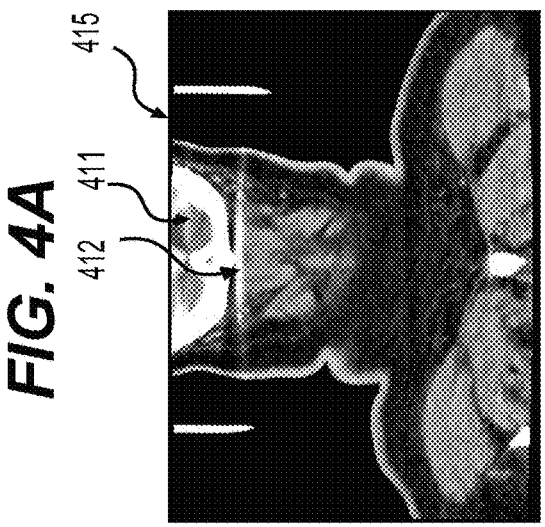
FIG. 4B shows an example of an axial view of the reconstructed image from the CBCT scan, according to an embodiment of the disclosure.

FIGS. 4A-4D show exemplary images 410, 415, 420, and 425 according to an embodiment of the disclosure. FIGS. 4A and 4B show the first coronal view 410 and a second coronal view 415 of a first object, for example, a first region of a body. In some embodiments, the first coronal view 410 is generated under optimal imaging conditions using an X-ray beam having the small cone angle and corresponds to artifact-minimized data. The second coronal view 415 is generated using an X-ray beam having the large cone angle and corresponds to artifact-exhibiting data. For example, areas 411 and 412 illustrate pronounced cone-beam artifacts that are not detectable in the first coronal view 410.

Figure 4D:
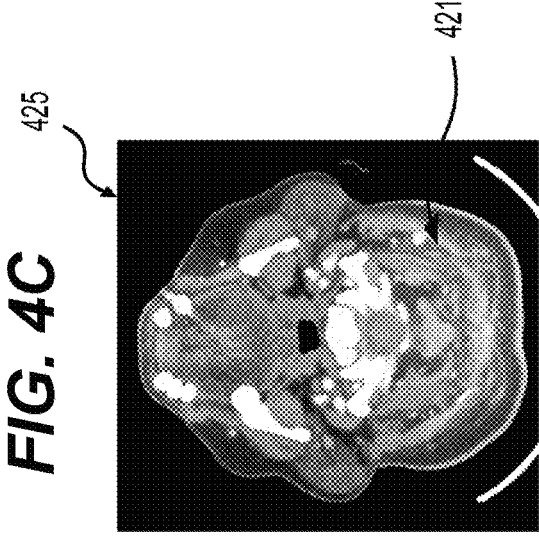
FIG. 4D shows an example of an axial view of the reconstructed image from the helical CT scan, according to an embodiment of the disclosure.

FIGS. 4C and 4D show a first axial view 420 and a second axial view 425 of a second object, for example, a second region of a body. In some embodiments, the first axial view 420 is generated under optimal imaging conditions an X-ray beam having using the small cone angle. The second axial view 425 is generated using an X-ray beam having the large cone angle. For example, area 421 illustrates cone-beam shading artifacts that are not detectable in the first axial view 420. Referring to FIGS. 4B and 4D, however, the cone-beam artifacts illustrated by the areas 411 and 412 in the coronal view are more pronounced than the cone-beam artifacts illustrated by the area 421 in the axial view. According to embodiments of the disclosure, 2D coronal views, such as the first coronal view 410 and the second coronal view 415 corresponding to the artifact-minimized data and the artifact-exhibiting data are included in a training dataset in step S112. In some examples, the first axial view 420 and the second axial view 425 are excluded from a training dataset in step S112. Further, in some embodiments, 2D sagittal views corresponding to artifact-exhibiting data and artifact-minimized data are also included in a training dataset in step S112.

Additional image processing methods can be included, for example, in the methods 110 and 300 to reduce training time. Certain imaging artifacts, such as cone-beam artifacts, vary slowly with respect to space, i.e., have low spatial frequency components. When the neural network trained in the method 110 is a CNN, a relatively large receptive field is used, for example, to account for the low spatial frequency components. According to aspects of the disclosure, an image is split into multiple sub-images that have a smaller number of pixels while a receptive field of each sub-image is comparable to a receptive field of the image. In some examples, the image is down-sampled to obtain the multiple sub-images, as described below. The respective sub-images are included in a training dataset, such as the training dataset generated using the method 110.

FIG. 5 shows a non-limiting example of pixels in an image 550 being down-sampled and subdivided into four smaller sub-images 521-524, according to an embodiment of the disclosure. For example, image 550 can be a 2D slice of a reconstructed image in a sagittal or coronal plane. In FIG. 5, the image 550 is down-sampled by a factor 2 in a first direction and a factor 2 in the second direction. In general, image 550 can be down-sampled by a factor N in a first direction and a factor M in the second direction, in which case N×M sub-images would be generated. When the image 550 is to be applied to a CNN (e.g., to train the CNN), the pixels can be grouped into respective 2-by-2 blocks, such as the first block 551, and the pixels within each block given an index from 1 to 4. All of the pixels having the same index are combined to form respective sub-images. For example, the pixel 551(1) from the pixel group 551 is shown in sub-image 521, and the pixel 551(2) from the pixel group 551 is shown in sub-image 522. Further, the pixel 551(3) from the pixel group 551 is shown in sub-image 523, and the pixel 551(4) from the pixel group 551 is shown in sub-image 524. Accordingly, all of the information from image 550 is preserved in the sub-images 521-524.

In addition to decreasing the number of pixels per sub-image by a factor of N×M (e.g., in FIG. 5, N=M=2), down-sampling also decreases the number of pixels per receptive field by a factor of N×M, resulting in a total decrease by a factor of $N^2 \times M^2$ for the number of multiplications to perform a convolutional layer on a sub-image as opposed to the original image. For example, FIG. 5 shows a 6-by-6 receptive field 552 for image 550. For sub-images 521-524, however, the corresponding receptive fields 552 (1)-(4) each have dimensions of 3-by-3 (i.e., $\frac{1}{4}^{th}$ the number of pixels as in image 552). When each sub-image can be applied to a neural network for down-sampled image, much fewer calculations are required. Further, during training, the neural network can converge more quickly to the optimal weighting coefficients between layers.

Accordingly, the image 550 is down-sampled into the four sub-images 521-524 having a lower image resolution than an image resolution of the image 550. In various embodiments, image resolution has a unit of $mm^2$ per pixel in a 2D image and $mm^3$ per pixel in a 3D image, where 1 mm is 1 millimeter. The sub-images 521-524 include the respective pixels indexed by 1, 2, 3, or 4. Referring to FIG. 5, a number of pixels in each second receptive field is ¼ of a number of pixels in the first receptive field 552, thus, training a CNN with sub-images is faster. Note that the second receptive field 552 in the original image 550, although including four time more pixels, represents a same physical area as is represented by each of the receptive field 552(1)-(4) in the sub-images 521-524.

Figure 6:
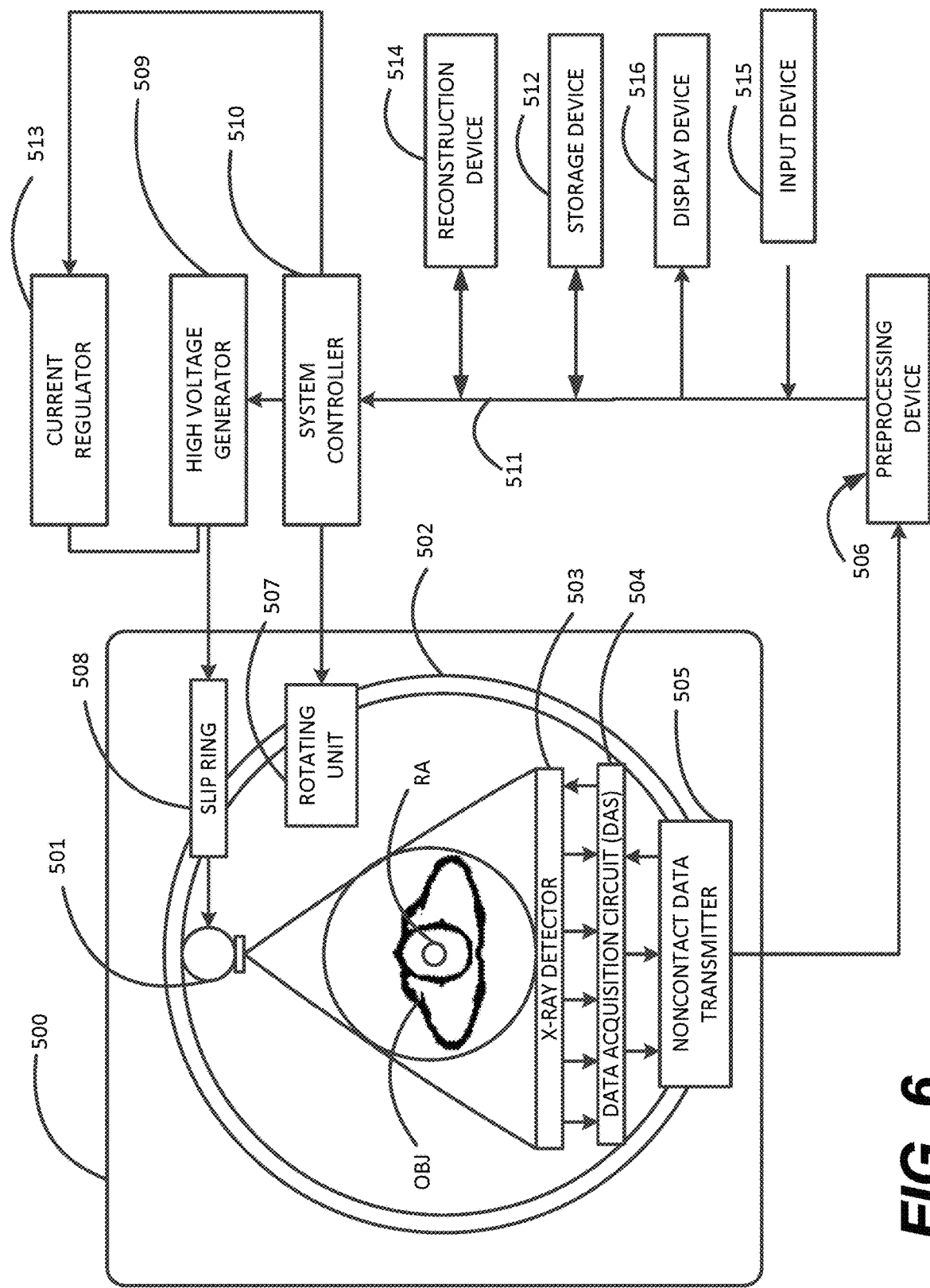
FIG. 6 shows a schematic of an implementation of a CT scanner, according to an embodiment of the disclosure.

FIG. 6 shows a schematic of an implementation of a CT scanner according to an embodiment of the disclosure. Referring to FIG. 6, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA (or an axis of rotation). A rotating unit 507 rotates the annular frame 502 at a high speed, such as 0.4 sec/rotation, while the object OBJ is being moved along the axis RA into or out of the illustrated page.

X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present disclosure can be applied to either type. The rotate/rotate type will be used as an example for purposes of clarity.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A memory 512 stores the resultant data, which is also called projection data at a stage immediately before reconstruction processing. The memory 512 is connected to a system controller 510 through a data/control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing, for example, various steps of the methods 110, 150, 200, and 300 for training a neural network and reducing imaging artifacts.

The reconstruction device 514 can execute various steps of the methods 110, 150, 200, and 300. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example.

Post-reconstruction processing performed by the reconstruction device 514 can include filtering and smoothing the image, volume rendering processing, and image difference processing as needed. The image reconstruction process can implement various of the steps of methods 110, 150, 200, and 300 in addition to various CT image reconstruction methods. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:
1. An apparatus, comprising:
processing circuitry configured to train a neural network by
obtaining a pair of reconstructed computed tomography (CT) images including an artifact-exhibiting image and an artifact-minimized image, the artifact-exhibiting image having a greater degree of artifacts than the artifact-minimized image, including
obtaining the artifact-minimized image by reconstructing the artifact-minimized image from first projection data, the first projection data being radiation data obtained using an X-ray beam that is less than a predefined angle threshold, and
simulating the artifact-exhibiting image from the artifact-minimized image, including forward projecting, using a CT scan configuration with the X-ray beam that is greater than the predefined angle threshold, the artifact-minimized image to generate second projection data from which the artifact-exhibiting image is generated;
forming a training dataset including the pair of reconstructed CT images;
applying the artifact-exhibiting image to the neural network to generate an output image having reduced artifacts with respect to the artifact-exhibiting image, the neural network including neuronal nodes connected by connections having weighting coefficients;
calculating a cost function representing a difference or disagreement between the output image and the artifact-minimized data;

updating the weighting coefficients in the neural network to optimize the cost function; and stopping, upon satisfying a predefined stopping criteria, the updating of the weighting coefficients, so that the neural network is then a trained neural.

2. The apparatus according to claim 1, wherein the processing circuitry is further configured to perform the forward projecting using a cone-beam scan configuration with the X-ray beam that is greater than the predefined angle threshold.

3. The apparatus according to claim 1, wherein the processing circuitry is further configured to perform the applying the artifact-exhibiting image to the neural network by partitioning the artifact-exhibiting image into two-dimensional (2D) slices corresponding to one or more of a coronal view and a sagittal view, applying each of the 2D slices to the neural network, which is a 2D convolutional neural network, to generate respective 2D output images, and combining the 2D output images to generate the output image, which is a three-dimensional (3D) image.

4. The apparatus according to claim 1, wherein the processing circuitry is configured to perform the obtaining the pair of reconstructed CT images by obtaining a pair of high-resolution (HR) reconstructed CT images including an HR artifact-exhibiting image and an HR artifact-minimized image, splitting the HR artifact-exhibiting image by a factor N in a first direction by a factor M in a second direction to generate a total number of N*M artifact-exhibiting sub-images, and splitting the HR artifacts-minimized image by the factor N in the first direction by the factor M in the second direction to generate a total number of N*M artifacts-minimized sub-images.

5. The apparatus according to claim 4, wherein the processing circuitry is configured to perform the splitting the HR artifact-exhibiting and splitting the HR artifacts-minimized image by one of selecting every Nth voxel in the first direction and every Mth voxel in the second direction for the HR artifact-exhibiting and the HR artifacts-minimized image, respectively, and transforming into a frequency domain and selecting a 1/N percentage of the low-frequency components in the first direction and a 1/M percentage of the low-frequency components in the second direction for the HR artifact-exhibiting and the HR artifacts-minimized image, respectively.

6. The apparatus according to claim 1, wherein the processing circuitry is further configured to:

acquire the artifact-exhibiting image by forward projecting the artifact-minimized image using a circular cone-beam scan configuration with the X-ray beam having a cone angle greater than the predefined angle threshold, to generate second projection data.

7. The apparatus according to claim 1, wherein the processing circuitry is further configured to:

reconstruct the artifacts-minimized image from projection data by performing a helical CT scan using an X-ray beam spanning less than a predefined angle threshold.

8. An apparatus, comprising:

processing circuitry configured to:

obtain an artifact-exhibiting diagnostic image having a computed tomography (CT) imaging artifact, obtain a the neural network including a plurality of layers having neuronal nodes connected by connections having weighting coefficients, the plurality of layers including an input layer receiving an input image and an output layer outputting an output image, the neural network being trained according to claim 1 to produce an output image that has less of the CT imaging artifact than the input image; and apply the artifact-exhibiting diagnostic image as the input image to the neural network to generate an artifact-minimized diagnostic image having less of the CT imaging artifact than the artifact-exhibiting diagnostic image.

9. The apparatus according to claim 8, wherein the processing circuitry is further configured to obtain the artifact-exhibiting diagnostic image, wherein the artifact-exhibiting diagnostic image is reconstructed from projection data of a cone-beam scan in which an X-ray beam has a cone angle greater than a predefined angle threshold, and the CT imaging artifact includes a cone-beam artifact.

10. The apparatus according to claim 8, wherein the processing circuitry is further configured to determine one or more scanning parameters used in a CT scan from which the artifact-exhibiting diagnostic image was reconstructed, the one or more scanning parameters being one or more of an anatomic structure to be imaged, a scanning protocol, and a diagnostic application, and select the neural network from a plurality of neural networks that are respectively categorized and trained according to the one or more scanning parameters, each of the plurality of neural networks being trained using a respective training datasets including images having the imaging artifact and being reconstructed from CT scans corresponding to a respective scanning parameter of the one or more scanning parameters.

11. The apparatus according to claim 8, wherein the processing circuitry is further configured to apply the artifact-exhibiting diagnostic image to the neural network by separating the artifact-exhibiting diagnostic image into a low-frequency image and a high-frequency image, the low-frequency image being smaller than the artifact-exhibiting diagnostic image by a factor N in a first direction and by a factor M in a second direction, applying the low-frequency image to the neural network to generate a low-frequency output image, and combining the low-frequency output image with the high-frequency image to generate the artifact-minimized diagnostic image.

12. The apparatus according to claim 8, wherein the processing circuitry is further configured to apply the artifact-exhibiting diagnostic image to the neural network by partitioning the artifact-exhibiting diagnostic image, which is a three-dimensional (3D) image, into two-dimensional (2D) slices corresponding to one or more of a coronal view and a sagittal view, applying each of the 2D slices to the neural network, which is a 2D convolutional neural network, to generate respective 2D output images, and combining the 2D output images to generate the artifact-minimized diagnostic image, which is a 3D image.

13. The apparatus according to claim 8, further comprising:

an X-ray source configured to radiate X-ray radiation that produces an X-ray beam having a cone angle that is greater than a predefined angle threshold;

a detector including a plurality of detector elements, the detector configured to detect the X-ray radiation from the X-ray source after the X-ray radiation has traversed through an object, and generate projection data representing an intensity of the X-ray radiation detected at the plurality of detector elements; and a memory device storing the trained neural network, which has been trained in advance.

14. A method, comprising:

obtaining a pair of reconstructed computed tomography (CT) images including an artifact-exhibiting image and an artifact-minimized image, the artifact-exhibiting image having a greater degree of artifacts than the artifact-minimized image, including obtaining the artifact-minimized image using an X-ray beam that spans a solid angle less than a predefined angle threshold, and simulating the artifact-exhibiting image from the artifact-minimized image, including forward projecting, using a CT scan configuration with the X-ray beam that is greater than the predefined angle threshold, the artifact-minimized image to generate simulated projection data from which the artifact exhibiting image is generated;

forming a training dataset including the pair of reconstructed CT images;

applying the artifact-exhibiting image to a neural network to generate an output image having reduced artifacts with respect to the artifact-exhibiting image, the neural network including neuronal nodes connected by connections having weighting coefficients;

calculating a cost function representing a difference or disagreement between the output image and the artifact-minimized data;

updating the weighting coefficients in the neural network to optimize the cost function; and stopping, upon satisfying a predefined stopping criteria, the updating the weighting coefficients, so that the neural network is then a trained neural network.

15. The method according to claim 14, wherein the forward projecting the artifact-minimized image includes, forward projecting the artifact-minimized image using a circular cone-beam scan configuration with the X-ray beam that is greater than the predefined angle threshold to generate the second projection data.

16. The method according to claim 14, wherein the applying the artifact-exhibiting image to the neural network further includes partitioning the artifact-exhibiting diagnostic image into two-dimensional (2D) slices corresponding to one or more of a coronal view and a sagittal view, applying each of the 2D slices to the neural network, which is a 2D convolutional neural network, to generate respective 2D output images.

17. A method, comprising:

obtaining an artifact-exhibiting diagnostic image having a computed tomography (CT) imaging artifact, obtaining a neural network including a plurality of layers having neuronal nodes connected by connections having weighting coefficients, the plurality of layers including an input layer receiving an input image and an output layer outputting an output image, the neural network being trained according to claim 14 to produce the output image that has less of the CT imaging artifact than the input image; and applying the artifact-exhibiting diagnostic image as the input image to the neural network to generate an artifact-minimized diagnostic image having less of the CT imaging artifact than the artifact-exhibiting diagnostic image.

18. The method according to claim 17, wherein the applying the artifact-exhibiting diagnostic image to the neural network further includes separating the artifact-exhibiting diagnostic image into a low-frequency image and a high-frequency image, the low-frequency image being smaller than the artifact-exhibiting diagnostic image by a factor N in a first direction and by a factor M in a second direction, applying the low-frequency image to the neural network to generate a low-frequency output image, and combining the low-frequency output image with the high-frequency image to generate the artifact-minimized diagnostic image.

19. A non-transitory computer readable storage medium including executable instructions, wherein the instructions, when executed by circuitry, cause the circuitry to perform the method according to claim 14.

* * * * *